United States Patent [19]

Fried

[11] Patent Number: 5,166,409

[45] Date of Patent: Nov. 24, 1992

[54] PREPARATION OF CARBOXYLIC ACID ESTERS

[75] Inventor: Herbert E. Fried, Houston, Tex.

[73] Assignee: Shell Oil Company, Houston, Tex.

[21] Appl. No.: 797,001

[22] Filed: Nov. 25, 1991

[51] Int. Cl.$^5$ ............................................. C07C 69/52
[52] U.S. Cl. ..................................... 560/205; 554/223
[58] Field of Search .......................... 560/205; 554/223

[56] References Cited

U.S. PATENT DOCUMENTS

| | | | |
|---|---|---|---|
| 2,093,695 | 9/1937 | Larson | 260/106 |
| 3,534,087 | 10/1970 | Leftin et al. | 260/491 |
| 3,641,120 | 2/1972 | Broderick et al. | 260/491 |
| 3,755,386 | 8/1973 | Wilke et al. | 260/410.9 R |
| 3,783,136 | 1/1974 | Inukai et al. | 260/410.9 R |
| 3,855,255 | 12/1974 | Dohr et al. | 260/410.9 R |
| 3,892,788 | 7/1975 | Knifton | 260/410.9 R |
| 4,009,203 | 2/1977 | Schmerlin | 260/497 R |
| 4,144,257 | 3/1979 | Kumobayashi et al. | 260/410.9 R |
| 4,506,095 | 3/1985 | Koermer | 560/205 |
| 4,822,911 | 4/1989 | Fried | 560/205 |

FOREIGN PATENT DOCUMENTS

| | | |
|---|---|---|
| 739208 | 9/1968 | Belgium . |
| 2044159 | 9/1970 | Fed. Rep. of Germany . |
| 3149979 | 12/1980 | Fed. Rep. of Germany . |
| 496265 | 7/1973 | South Africa . |
| 8100846 | 9/1979 | World Int. Prop. O. . |

OTHER PUBLICATIONS

Akermark et al., "Eutectic Potassium-Sodium-Aluminum Chloride as a Mild Catalyst for Ene Reactions: Simple Synthesis of the Sex Pheromone from Douglas Fir Tussock Moth," J. Org. Chem., vol. 43, No. 22, 1978, 4387.

Snider, "The Lewis Acid Catalysis of Ene Reactions," vol. 39, No. 2, 1972, p. 255.

*Primary Examiner*—Paul J. Killos
*Attorney, Agent, or Firm*—Pamela J. McCollough

[57] ABSTRACT

The present invention relates to a process for the preparation of higher alkyl acrylic acid esters which comprises contacting and reacting under ene reaction conditions one or more olefins with one or more alkyl acrylic acid esters in the presence of a catalytically effective amount of a mixture of aluminum chloride and ethylaluminum dichloride.

9 Claims, No Drawings

PREPARATION OF CARBOXYLIC ACID ESTERS

FIELD OF THE INVENTION

This invention relates to a process for the preparation of carboxylic acids esters, which are known to find use, for example, in formulating medicines, ointments, cosmetics and lubricating oils, as soaps, as plasticizers, as solvents, and as chemical intermediates. More particularly, this invention relates to a reaction process for the preparation of higher alkyl acrylic acid esters, in which olefins are contacted and reacted with lower alkyl acrylic acid esters, in the presence of a catalyst comprising a mixture of aluminum chloride and ethylaluminum dichloride.

BACKGROUND OF THE INVENTION

Various catalysts are known to promote the "ene reaction" of olefins with alpha-, beta-unsaturated carboxylic acid esters for the production of unsaturated carboxylic acid esters. For instance, U.S. Pat. No. 3,783,136 and German Offenlengungsschrift both describe the use of $AlCl_3$ and $AlBr_3$ as catalysts for such reactions. U.S. Pat. No. 4,506,095 describes the reaction of linear alpha-olefins with alkyl acrylates catalyzed by an organometallic catalyst of the formula $R_n-Al-X_{3-n}$, wherein R is an organic radical containing between about 1 and 12 carbon atoms, n is the integer 1 or 2, and X is chlorine or bromine. U.S. Pat. No. 3,641,120 describes the reaction of an ester with an olefin in the presence of a combination of a manganic carboxylic acid salt or oxide with a zirconyl carboxylic acid salt or zirconium oxide. The publication by B. R. Snider on J. Org. Chem., Vol. 39, No. 2 (1972), p. 255, refers generally to Lewis acid catalysts for ene reactions, but illustrates only the use of aluminum chloride and zinc bromide. U.S. Pat. No. 3,855,255 describes the reaction of carboxylic acid esters by reacting diolefins with methacrylate esters in the presence of an organometallic complex of zero-valent nickel and an electron donor. U.S. Pat. No. 2,093,695 discloses preparation of carboxylic acid esters by reaction of acyloxy compounds with olefinic hydrocarbons catalyzed by activated charcoal, inorganic acids, the halogens and various halides of calcium, boron, cadmium, zinc, calcium and potassium. Co-pending Application Ser. No. 510,309, filed Apr. 17, 1990, U.S. Pat. No. 5066829 describes an ene reaction catalyzed by tantalum pentachloride. Akermark et al (J. Org. Chem., Vol. 43, No. 22 (1978), 4387) have reported that the eutectic mixture of $AlCl_3$ NaCl, and KCl is a superior ene reaction catalyst. U.S. Pat. No. 3,892,788 teaches a ligand-stabilized Pt(II) dihalide complex combined with a Group IVB metal halide as a catalyst for such ene reactions. South African Patent 496,265 describes one such reaction catalyzed by various organometal compounds. According to German Offenlegungsschrift 2044159, a reaction between acrylic acid esters and dienes is catalyzed by an organometallic complex of zero-valent iron and a triaryl compound of an element of Group V. U.S. Pat. Nos. 3,755,386 and 4,144,257 and Belgian published application 739,208 describe similar reactions using complexes of Group VIII compounds, as well as various compounds and complexes of iron, nickel and cobalt. U.S. Pat. Nos. 4,009,203 and 3,534,087, German Offenlegungsschrift 3149979 and World Patent No. 8100846 describe related reactions of acids and olefins catalyzed by and acyloxystannic trihalide or a perfluorosulfonic acid resin or a crystalline metal silicate or an aluminum silicate containing a Group VIII metal compound and a polyvalent metal halide.

It has been found that a co-catalyst comprising a mixture of aluminum chloride and ethylaluminum dichloride exhibits the high activity which would be obtained by using aluminum chloride alone as well as serving to suppress the formation of alkyl chloride byproducts which is characteristic of conventional aluminum chloride-catalyzed processes.

SUMMARY OF THE INVENTION

The present invention relates to the reaction of alkyl esters of acrylic acid with olefins promoted by a catalyst comprising a catalytically effective amount of a mixture of aluminum chloride and ethylaluminum dichloride.

DESCRIPTION OF THE PREFERRED EMBODIMENTS

The process of the present invention is applicable to the reaction of an olefin (formula I) with an alkyl ester of acrylic acid (formula II) for the preparation of a higher alkyl acrylic acid ester compound (formula III), as represented by the following equation:

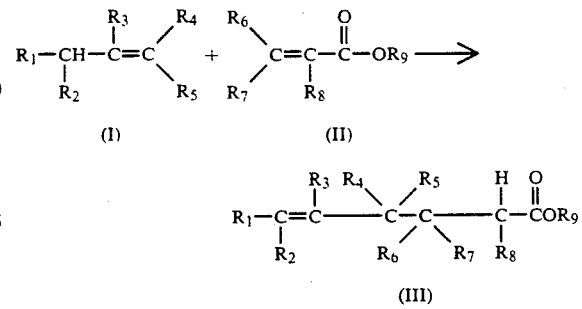

wherein $R_1$ is alkyl, $R_2$, $R_{3l}$, $R_4$, $R_5$, $R_6$, $R_7$ and $R_8$ are each individually selected from the group consisting of hydrogen and alkyl moieties, and $R_9$ is an alkyl group.

The reactant olefins are acylic alkenes, and suitably encompass diolefins, particularly non-conjugated diolefins. In general, the olefin reactant molecule may have from 3 to about 40 carbon atoms. Preferably, the invention is applied to a liquid phase reaction involving olefins in the carbon number range of from about 6 to about 30, inclusive. In one embodiment, preference can be expressed for an olefin reactant carbon number in the range of from about 8 to about 20, inclusive, particularly a carbon number in the range of from about 14 to about 18, inclusive. The olefin molecule is suitably either branched or linear and may have either an alpha-or an internal double bond position. Olefins having a vinylidene structure have been found to be generally more reactive than olefins having a linear structure. More highly branched olefins, produces for example by oligomerization of polypropylene and butylene, are very suitable reactants. Linear internal olefins have generally been observed to have relatively low reactivity and to generate substantial amounts of side products.

Mixed olefin reactants are also very suitable. However, as recognized in U.S. Pat. No. 4,822,911, olefins of different molecular structure may have different reactivities under certain process conditions. Linear olefins having an internal double bond position have also been observed to react more slowly than olefins of other structures.

The lower alkyl esters of acrylic acid which are employed as reactants in this invention are suitably acrylates and alkyl-substituted acrylates represented by formula II above. Mixtures of different alkyl acrylic acid esters are suitable reactants.

The $R_9$ substituent of the ester reactant molecule is preferably an alkyl group having a carbon number of up to about 30, more preferably one having from 1 to about 15 carbon atoms, and most preferably one having from 1 to about 8 carbon atoms. The $R_6$ $R_7$ and $R_8$ substitutents each independently represent either a hydrogen atom or an alkyl group, preferably a hydrogen atom or a lower, i.e., $C_1$ to $C_4$, alkyl group. If desired, the acrylate ester reactant may be suitably substituted with one or more non-hydrocarbyl substituents which do not substantially affect the intended reaction. As an example, one or more of the $R_6$, $R_7$ and $R_8$ substituents is suitably a halogen or a halogen substituted alkyl group.

Specific examples of alkyl acrylic acid ester reactants include methyl acrylate, ethyl acrylate, n-propyl acrylate, isopropyl acrylate, n-butyl acrylate, isobutylacrylate, tertiary butyl acrylate, n-octyl acrylate, isooctyl acrylate, 2-ethylhexylacrylate, n-tetradecylacrylate, n-hexadecyl acrylate and methyl alpha-chloroacrylate. In one respect, alkyl acrylic acid esters having from 4 to about 8 total carbon atoms are particularly preferred ester reactants. In another respect, preference can be expressed for ester reactants in which the $R_6$, $R_7$ and $R_8$ substituents are each hydrogen. Very good results have been obtained with methyl acrylate.

Also suitable as alkyl acrylic acid ester reactants in the process of the present invention are the dimers, trimers, and other oligomers of the indicated acrylic acid esters, such as, for example, trimethylolpropane triacrylate, 1,6-hexanediol diacrylate, and the like.

The relative proportions of the olefin reactant and the ester reactant are not critical to the invention. However, preference can be expressed for a molar ratio of olefin to ester reactant in the range of from about 1:30 to about 30:1. A molar ratio of olefin to ester in the range of from about 1:10 to about 10:1 is considered more preferred, and a ratio in the range of from about 5:1 to about 1:1 is considered most preferred in order to obtain good conversion to the desired product, while minimizing formation of side products.

For purposes of the process of this invention, the olefin reactant and the alkyl acrylic acid ester reactant are contacted, in the liquid phase, in the presence of a catalytically effective amount of a mixture of aluminum chloride and ethyl aluminum dichloride. The contact and reaction may take place in either a batch or continuous mode. Suitably the mixture contains from about 0.1 mole percent to about 15 mole percent, preferably from about 2 mole percent to about 7 mole percent of aluminum chloride, and from about 0.1 mole percent to about 10 mole percent, preferably from about 0.1 mole percent to about 5 mole percent of ethyl aluminum dichloride, basis the number of moles of starting olefin. In a preferred embodiment, the mixture contains from about 3 mole percent to about 7 mole percent of aluminum chloride and from about 0.5 mole percent to about 2 mole percent of ethyl aluminum dichloride, basis the number of moles of starting olefin.

In addition to the reaction and catalyst, it has been found that, while not critical, it is useful to add to the reaction mixture a small quantity of an antioxidant material such as hydroquinone, in order to inhibit free-radical initiated polymerization reactions involving the acrylate esters.

The present invention primarily relates to the use of the aluminum chloride/ethylaluminum dichloride catalyst. In general, the process can otherwise be practiced under conditions characteristic of other ene reaction processes, although certain preferences can be expressed. Thus, depending on the reactivity of the olefin, the process is suitably carried out at a temperature in the range of from about 0° C. to about 300° C., preferably in the range of from about 40° C, to about 220° C., and more preferably in the range of from about 60° C. to about 150° C. pressure is not a critical variable in the process of the invention, although it is desirable that the pressure be sufficient to maintain the olefin and ester reactants substantially in the liquid phase. Operation at pressures between about 0 psig and about 1000 psig are very suitable, although higher pressures, e.g., 2000 psig or greater, are also suitable. If desired, the process can be carried out using a lower carbon number olefin reactant predominantly in the vapor phase under process conditions, and a liquid phase ester reactant. In a preferred embodiment, the reaction is stopped when the ene product is no longer being formed as the selectivity is diminished when the reaction is allowed to continue past that point.

The process of the invention can be practiced in the presence of a reaction solvent such as, for example, benzene, toluene, hexane, carbon tetrachloride, ethylene chloride, ethyl acetate or other solvents recognized in the art for use in ene reactions. Solvents often enhance the reaction rate, however, solvents are not necessary for the reaction to proceed and they are inconvenient to remove from the product. Accordingly, it is generally preferred that the process be carried out in the absence of added reaction solvents.

The contact/reaction step converts the reactants, in whole or in part, to higher alkyl acrylic acid ester adducts of the olefins. The product comprises the higher alkyl acrylic acid ester adducts of the olefins represented by formula III above, as well as other higher alkyl acrylic acid ester adduct isomers. Adducts of two or more ester molecules and one olefin molecule may also be produced, particularly when the process is practiced with an excess of ester reactant. Ene reactions of olefins with acrylate esters are known to produce side products including diesters, dimers, and products from catalyst decomposition.

The present invention is, in one respect, useful for the addition of alkyl acrylic acid esters to linear internal olefin molecules.

The reaction may be terminated by depletion of one or both of the reactants, or upon cooling of the reaction mixture, e.g., to a temperature of about 0° C., depending on the reactivity of the starting olefin. Either during or following termination of the reaction, the product mixture is preferably treated for separation, e.g., by filtration, of catalyst and/or catalyst residues. Generally the catalyst is at least partially soluble in the reaction mixture. To extract catalyst and catalyst residues from solution, it has been found that it is useful to wash the reaction mixture with an aqueous acid solution, e.g., with an equal volume of a 1 to 10 percent by weight aqueous sulfuric acid solution. This extraction technique is further described in the commonly-assigned copending application, Ser. No. 07/510,311, filed Apr.

17, 1990, the disclosure of which is incorporated herein by this reference.

Separation of the higher alkyl acrylic acid ester products from unreacted olefin and/or ester starting materials can be accomplished by distillation or by other procedures known in the art for the processing of ene reaction products.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of the invention is further described with reference to the following examples, which are intended to be illustrative of certain embodiments of the invention without limiting the invention's broader scope.

Illustrative Embodiments

Example 1

A process according to the invention was carried out for the reaction of methyl acrylate with a $C_{13}/C_{14}$ internal olefin reactant having primarily a linear carbon structure. For this purpose, 0.67 grams of aluminum chloride ($AlCl_3$), 20 grams of the olefin mixture, and 0.51 grams of a 25% solution of ethylaluminum dichloride ($EtAlCl_2$) in hexane were added to a 100 milliliter autoclave under a nitrogen atmosphere and contacted with 2.2 grams of methyl acrylate stabilized with hydroquinone. The autoclave was then charged with 100 psi $N_2$ and the reaction was commenced according to the parameters presented in Table I. The results of this experiment are presented in Table II.

Examples 2 and 3

Examples 2 and 3 were carried out in a manner similar to Example 1 according to the parameters presented in Table I. The results of these experiments are shown in Table II below.

Comparative Example A

Comparative Example A was carried out in a manner similar to Example 3 except that no ethylaluminum dichloride was added and the olefin to methyl acrylate molar ratio was 1.0:0.5. Other parameters for this example, together with the process results, are presented in Tables I and II below.

Comparative Example B

Comparative Example B was carried out in a manner similar to Example 3 except that the reaction time was 16 hours instead of 2 hours. Other parameters for this example, together with the process results, are presented in Tables I and II below.

Comparative Example C

Comparative Example C was carried out in a manner similar to Example 1 except that no aluminum chloride was added and the reaction time was 16 hours. Other parameters for this example, together with the process results are presented in Table I and II below.

As can be seen in the Tables below, the co-catalyst system of aluminum chloride and ethylaluminum dichloride successfully surpresses alkyl chloride formation without adversely affecting conversion levels. These results also show that the reaction time is an important variable to monitor as extensive reaction times (i.e., times in which heating is allowed to continue after the reaction is substantially complete) afford proportionally higher amounts of alkyl chlorides. The results also show that while ethylaluminum dichloride alone may not afford the alkyl chloride side products, even with extensive reation times, this more expensive catalyst is substantially less reactive than either aluminum chloride, or the aluminum chloride/ethylaluminum dichloride mixtures.

TABLE I

| Example No. | $AlCl_3$/$EtAlCl_2$ Molar Ratio (Basis Olefin) | Olefin/ Methyl Acrylate Molar Ratio | Rxn Time (hr.) | Rxn Temp. (°C.) |
|---|---|---|---|---|
| 1 | 0.05/0.01 | 1/0.25 | 6 | 120 |
| 2 | 0.05/0.25 | 1/1 | 6 | 140 |
| 3 | 0.05/0.05 | 1/0.4 | 2 | 140 |
| Comp. A | 0.05/0 | 1/0.5 | 2 | 140 |
| Comp. B | 0.05/0.05 | 1/0.4 | 16 | 140 |
| Comp. C | 0/0.05 | 1/0.4 | 16 | 140 |

TABLE II

| Example No. | % Olefin Conversion | Selectivity to 1:1 Adduct (%) | Selectivity to Alkyl Chloride (%) |
|---|---|---|---|
| 1 | 17 | >99 | <1 |
| 2 | 23.8 | >99 | <1 |
| 3 | 19 | >99.9 | ND |
| Comp. A | 26.5 | 78.1 | 21.9 |
| Comp. B | 23.8 | 73.5 | 26.5 |
| Comp. C | 10 | >99.9 | ND |

What is claimed is:

1. A process for the preparation of higher alkyl acrylic acid esters which comprises contacting and reacting under ene reaction conditions one or more olefins with one or more alkyl acrylic acid esters in the presence of a catalytically effective amount of a mixture of aluminum chloride and ethylaluminum dichloride.

2. The process of claim 1 wherein said mixture comprises for about 0.1 mole percent to about 15 mole percent of aluminum chloride and from about 0.1 mole percent to about 10 mole percent of ethylaluminum dichloride.

3. The process of claim 2 wherein said mixture comprises for about 2 mole percent to about 7 mole percent of aluminum chloride and from about 1 mole percent to about 5 mole percent of ethylaluminum dichloride.

4. The process of claim 1 wherein the olefins have carbon numbers in the range of from about 6 to about 30, inclusive.

5. The process of claim 4 wherein the reactant alkyl acrylic acid esters have carbon numbers in the range of from about 4 to about 8, inclusive.

6. The process of claim 5 wherein the olefins have carbon numbers in the range of from about 8 to about 20, inclusive.

7. The process of claim 6 wherein the olefins have carbon numbers in the range of from about 14 to about 18, inclusive.

8. The process of claim 1, wherein the contact and reaction take place at a temperature in the range of from about 40° C. to about 220° C. and in the presence of from about 0.1 percent by mole to about 15 percent by mole of a mixture of aluminum chloride and from about 0.1 mole percent to about 10 mole percent of ethylaluminum dichloride.

9. The process of claim 1, wherein the contact and reaction take place at a temperature in the range of from about 60° C. to about 150° C. and in the presence of from about 2 percent by mole to about 7 percent by mole of a mixture of aluminum chloride and from about 1 mole percent to about 5 mole percent of ethylaluminum dichloride.

* * * * *